United States Patent [19]

Piosenka et al.

[11] Patent Number: 5,359,444
[45] Date of Patent: Oct. 25, 1994

[54] AUTO-FOCUSING OPTICAL APPARATUS

[75] Inventors: Gerald V. Piosenka; Peter J. Leahy, both of Scottsdale, Ariz.

[73] Assignee: Motorola, Inc., Schaumburg, Ill.

[21] Appl. No.: 996,531

[22] Filed: Dec. 24, 1992

[51] Int. Cl.⁵ .............................................. G02F 1/137
[52] U.S. Cl. ........................................ 359/94; 359/86; 351/169
[58] Field of Search .................. 359/37, 38, 54, 86, 359/94; 351/54, 55, 158, 168, 169, 176

[56] References Cited

U.S. PATENT DOCUMENTS

| | | | |
|---|---|---|---|
| 4,300,818 | 11/1981 | Schachar | 359/94 |
| 4,601,545 | 7/1986 | Kern | 359/44 |
| 4,756,605 | 7/1988 | Okada et al. | 359/94 |
| 5,066,301 | 11/1991 | Wiley | 359/94 |

FOREIGN PATENT DOCUMENTS

| | | | |
|---|---|---|---|
| 0237610 | 9/1989 | Japan | 359/319 |
| 2170613 | 8/1986 | United Kingdom | 351/158 |

OTHER PUBLICATIONS

Kowel et al., "Focusing by electrical modulation of refraction in a liquid crystal cell", Applied Optics, vol. 23, No. 2, Jan. 15, 1984.

*Primary Examiner*—William L. Sikes
*Assistant Examiner*—Huy Mai
*Attorney, Agent, or Firm*—Eugene A. Parsons

[57] ABSTRACT

Eyeglasses including lenses that contain liquid crystal nematic materials with variable refractive indexes. A voltage is applied across the materials to change the refractive index in accordance with a measured distance so that the lenses are always automatically focused as the operator looks at objects different distances away. The distances are measured by an infrared ranging system included in the glasses, which system changes the voltage applied to the material in accordance with changes in distance.

9 Claims, 5 Drawing Sheets

AUTO-FOCUSING OPTICAL APPARATUS

The present invention pertains to optical apparatus, such as eyeglasses and the like, and more specifically to optical apparatus capable of automatically focusing in a variety of circumstances.

BACKGROUND OF THE INVENTION

Variable focus optics are required in a number of applications. For most of these situations mechanical movement of the lens is required to change the focal point. In spectacles this is not practical and multi-focus lenses are used. A good example of multi-focal lenses is the bifocal lens which corrects for presbyopia with a + diopter lens. Since the accommodation range is reduced with age, this requires frequent change in the refractive prescription. In addition, the transition between the − diopter correction for myopia and the + diopter correction for presbyopia leaves certain focal ranges out of focus. Multi-focal lenses, such as trifocal lenses, attempt to correct for this limitation with limited success.

In many other optical applications the resolution is limited by how rapidly the focal length can be corrected. The input optical waveform may be distorted by the medium refractive variations. In this situation the focal length and/or refractive correction should be changed dynamically as a function of the time varying distortion. Electro mechanical methods have been used for this application, however, they are primarily applied to reflective optical systems.

SUMMARY OF THE INVENTION

It is a purpose of the present invention to provide new and improved apparatus and methods for automatically focusing optical apparatus.

It is a further purpose of the present invention to provide new and improved apparatus and methods for automatically focusing optical apparatus quickly and accurately.

It is a further purpose of the present invention to provide new and improved apparatus and methods for automatically focusing optical apparatus, and especially eyeglasses and the like.

It is a further purpose of the present invention to provide new and improved apparatus and methods for automatically focusing and otherwise compensating eyeglasses and the like for changes in the operators vision.

The above described problems and others, as well as the above purposes and others, are realized in auto focusing optical apparatus including an optical lens having a focal length determined by a refractive index thereof and containing electrically alterable material positioned to alter the refractive index of the optical lens in response to a voltage applied thereto, and a pair of electrical terminals coupled to the material and designed to have applied thereto a voltage so as to produce a predetermined alteration of the refractive index of the lens.

The above described problems and others, as well as the above purposes and others, are further realized in auto focusing optical apparatus comprising eyeglasses including a frame and a pair of optical lenses mounted in the frame, each optical lens including an optically transparent, hollow, lens shaped shell filled with liquid crystal nematic material positioned to alter the refractive index of the optical lens in response to a voltage applied thereto, and a pair of electrical terminals coupled to the liquid crystal nematic material and designed to have applied thereto a voltage so as to produce a predetermined alteration of the refractive index of the lens, and a computer system mounted in the frame with the electrical terminals of each optical lens being connected to the computer system, the computer system being programmed to apply to the electrical terminals of each optical lens a voltage so as to produce a predetermined alteration of the refractive index of each of the optical lenses.

BRIEF DESCRIPTION OF THE DRAWINGS

Referring to the drawings.

DESCRIPTION OF THE PREFERRED EMBODIMENT

Figure 1:
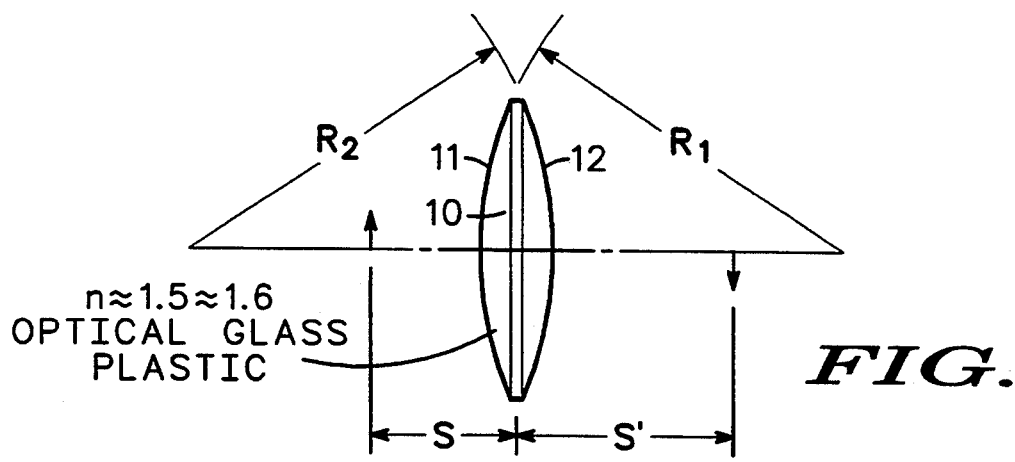
FIG. 1 is an optical diagram illustrating the focal length of a thin lens.

FIG. 1 is an optical diagram illustrating the focal length of a thin lens 10. Lens 10 has a first convex surface 11 with a radius of curvature $R_1$ and a second convex surface 12 with a radius of curvature $R_2$. The distance from an object being viewed to the center of lens 10 is designated S and the distance from the center of lens 10 to the focal point is designated S'. The following equation defines the focal length f of lens 10:

$$1/f = 1/S + 1/S'$$

Also, focal length f can be defined in terms of lens 10 as:

$$1/f = (n-1)\{1/R_1 - 1/R_2\}$$

where n equals the refractive index of the material forming lens 10. Generally, the refractive index of optical glass or optical plastic is in the range of 1.5 to 1.6. Thus, it can be seen that a change in the refractive index directly changes the focal length f.

Figure 2:
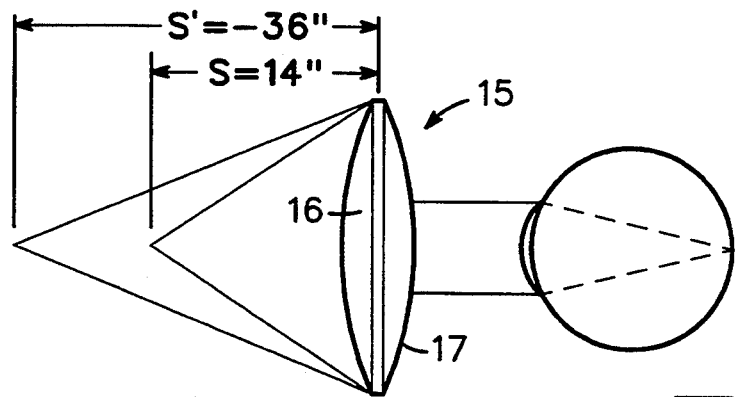
FIG. 2 is an optical diagram illustrating lens requirements for far-sighted or presbyopia.

FIG. 2 is an optical diagram illustrating, generally, lens requirements for far-sighted or presbyopia type eyes. In this specific situation, a complex lens 15 is formed, basically, of a first convex lens 16 with a flat rear surface and a second convex lens 17 with a flat front surface mounted parallel and in juxtaposition to the flat surface of lens 16. An object (a book or the like) positioned in front of lens 15 a normal reading distance S, which is generally 14 inches, appears to be at the focal point S', or approximately 36 inches in front of lens 15 . Here the focal length is:

$$1/f = 1/S + 1/S' = 1/14 - 1/36 = 0.0437$$

Thus, lens 15 is a converging lens with a 32.9 inch focal length. In terms of the art, a diopter equals 1/f in meters. Thus, converting the focal length of lens 15 to diopters, 22.9/39.37 equals 0.58 meters and 1/0.58 equals +1.7 diopters . Normal reading glasses range from 1 to 3 diopters.

Figure 3:
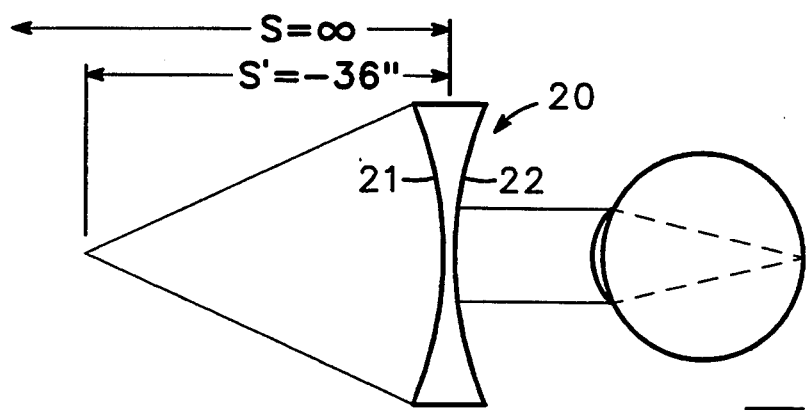
FIG. 3 is an optical diagram illustrating lens requirements for near-sighted.

FIG. 3 is an optical diagram illustrating lens requirements for near-sighted type eyes. In this specific situation, a complex lens 20 is formed with a front concave surface 21 and rear concave surface 22. An object, which is positioned in front of lens 15 sufficiently far to be considered an infinite distance S, appears to be at the focal point S', or approximately −36 inches in front of lens 20. For lens 20 the focal length is:

$$1/f = 1/S + 1/S' = 1/- 1/-36 = 0.0277$$

Thus, lens 20 is a diverging lens with a diopter of −1.09. In general, for near sighted presbyopic people, lens 20 must vary in a range of −1 to 2 diopters for full accommodation.

Figure 4:
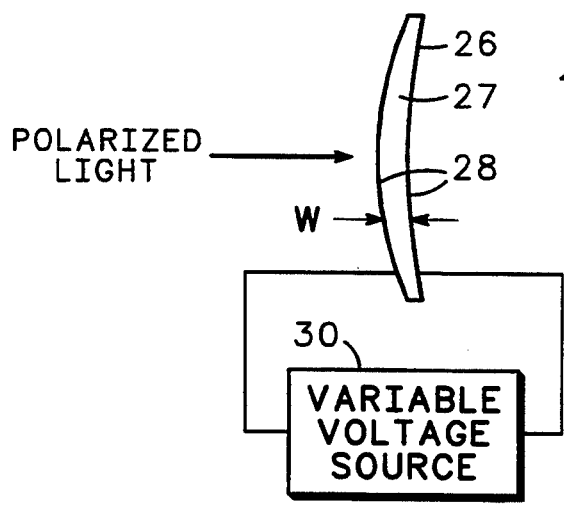
FIG. 4 is a semi-schematic view of a lens adapted to be used in an auto focusing lens system in accordance with the present invention.

FIG. 4 is a semi-schematic view of a lens 25 adapted to be used in an auto focusing lens system in accordance with the present invention. Lens 25 includes an optically transparent, hollow, lens shaped shell 26 filled with a liquid optically anisotropic material 27. Generally, shell 26 is formed of an optically clear plastic material with a substantially uniform thickness and a width w of approximately 20 to 50 microns. Material 27 is introduced through an opening along the edge, which opening is later sealed by any convenient means. Typical examples of liquid optically anisotropic material 27 are liquid crystals that have a nematic structure, such as, for example, p-methoxybenzyli- dene-p-n-butylaninine, otherwise known as MBBA, or.p-n-pentyl-p-cyanobiphenyl, otherwise known as PCB. An electrode 28, which may be for example some of the well known transparent conductors, is affixed to each major surface of lens 25 and a variable voltage source 30 is connected therebetween.

Figure 5:
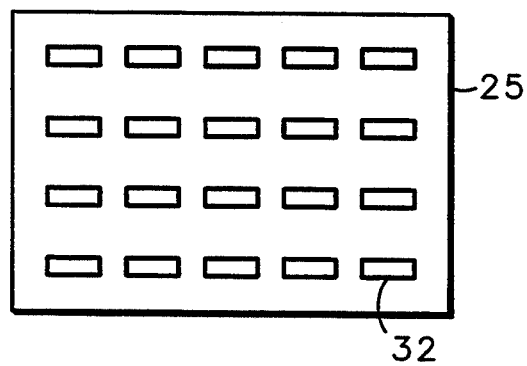
FIGS. 5 and 6 illustrate, generally, the operation of the lens of FIG. 4.
Figure 6:
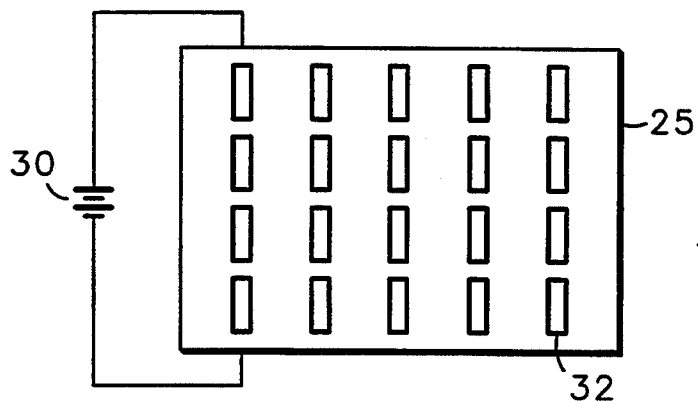

In liquid crystal nematic materials, the nematic phase is the physical mechanism that allows a change in the refractive index of the material. The nematic material is composed of rod shaped molecules 32, generally as illustrated diagrammatically in FIG. 5. The directional orientation of rod shaped molecules 32 is responsible for birefringence and is therefore optically anisotropic. Birefringence is the splitting of a light ray into the ordinary and extraordinary rays when it enters unaxial materials. In FIG. 5, molecules 32 are oriented generally horizontally and have a refractive index of approximately 1.2. By applying an electric field, with low voltage source 30, across material 27 as illustrated in FIG. 6, molecules 32 are caused to rotate and become parallel with the E field, which in this instance is approximately ninety degrees. In this orientation of molecules 32, the refractive index is uniformly changed to approximately 1.6. In the above described materials, MBBA and PCB, the birefringent change is achieved with a 4 volt change in the electric field. The two materials have negative and positive anisotropic characteristics, respectively. Typical values of the refractive index for suitable liquid crystal materials may range as high as 1.8 or more.

Figure 7:
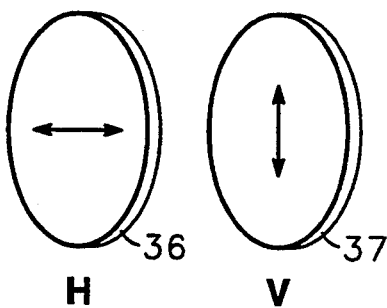
FIG. 7 illustrates another lens adapted to be used in an auto focusing lens system in accordance with the present invention.

In a simple lens, such as lens 25, the change in refractive index produces an effect which is dependent upon the polarization of light passing therethrough. However, a complex lens, such as lens 35 illustrated in FIG. 7, can be fabricated to be polarization independent. In this embodiment a pair of similar lenses, 36 and 37 are positioned coaxially in parallel juxtaposition and lens 37 is rotated axially ninety degrees, relative to lens 36. Thus, lens 36 is polarized horizontally and lens 37 is polarized vertically, which results in a combination, or complex, lens which is polarization independent.

Figure 8:
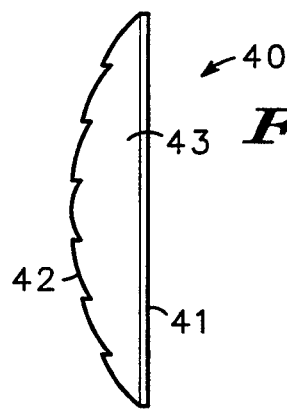
FIG. 8 illustrates still another lens adapted to be used in an auto focusing lens system in accordance with the present invention.

FIG. 8 illustrates a lens 40 adapted to be used in an auto focusing lens system in accordance with the present invention. Lens 40 is an optically transparent, hollow, lens shaped shell 41 filled with liquid crystal nematic material similar to those described previously. In this specific embodiment, however, one wall 42 of shell 41 is a Fresnel lens. Since the Fresnel lens forming wall 42 is preformed to provide some desired focal length or other desired feature, shell 40 is formed with a smaller width and less liquid optically anisotropic material 43. A smaller volume of material 43 reduces the reaction time (refractive index change) and reduces the amount of light lost in lens 40. Thus, the Fresnel lens, while increasing the cost somewhat and rendering the lens less adaptable to other situations, improves the quality.

Figure 9:
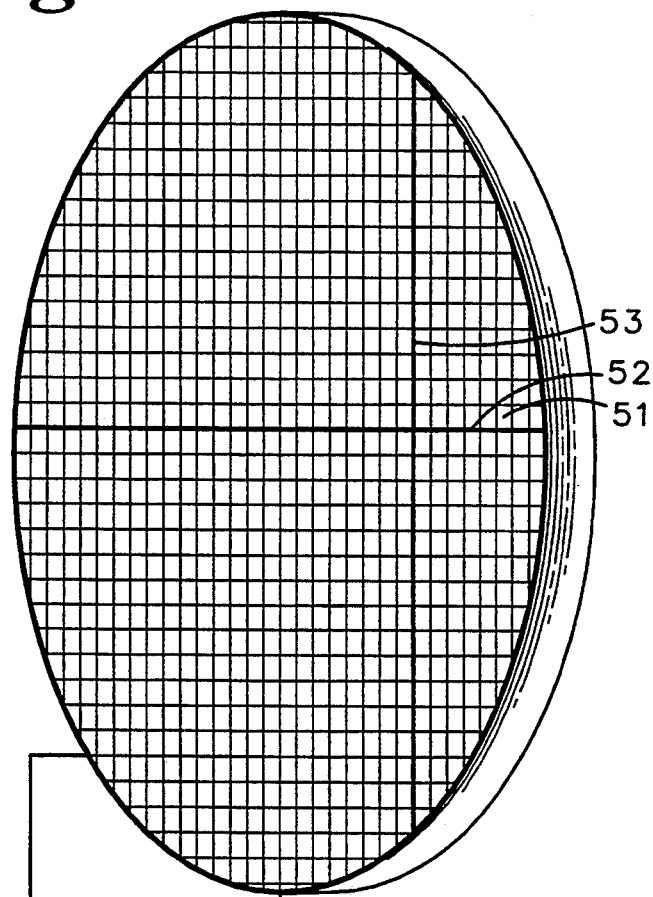
FIG. 9 illustrates still another lens adapted to be used in an auto focusing lens system in accordance with the present invention.
Figure 10:
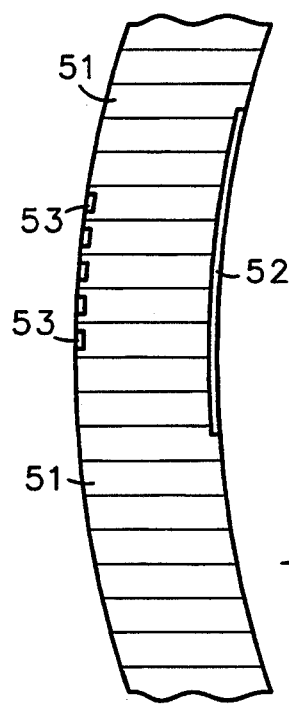
FIG. 10 is a semi-schematic, cross-sectional view of the lens of FIG. 9, generally illustrating the operation thereof.

FIG. 9 illustrates a pixel based lens 50 adapted to be used in an auto focusing lens system in accordance with the present invention. In this embodiment, lens 50 is formed of a plurality of individual, optically transparent pixel regions 51. A pixel region 51 of lens 50 is defined by the presence of two opposing transparent electrically conductive areas 52 and 53 on the interior of hollow lens 50. Opposing conductive areas 52 and 53 are provided with individual electrical contacts to enable the impression of an electrostatic field between the two surfaces. The electrostatic field acts on the nematic material suspended within hollow lens 50 to form a localized change in the index of refraction of the nematic material within the confines of each pixel region 51. The plurality of pixel regions 51 are formed into a continuous lens structure as illustrated in an enlarged cross-sectional view in FIG. 10. Pixel regions 51 are formed into rows and columns for convenience of operation. A plurality of horizontal transparent conductors 52 are connected, one each, to each row of pixel regions 51 and a plurality of vertical transparent conductors 53 are connected, one each, to each column of conductors on an opposite side thereof. Therefore, a matrix is formed in which the refractive index of any specific pixel region 51 can be changed by addressing the attached horizontal conductor 52 and the attached vertical conductor 53. In FIG. 10, lines illustrated between adjacent pixel regions 51 represent field fringing, which makes a smooth transition between adjacent pixel regions 51.

A matrix drive source 55 is attached to the pluralities of horizontal and vertical conductors 52 and 53 to provide the desired drive to pixel regions 51. Because pixel regions 51 are much smaller and contain relatively small quantities of liquid optically anisotropic material, the voltage required to provide the change is relatively small, generally in a range of 0.5 to 4 volts, and the change occurs very rapidly, generally in less than 5 milliseconds. Controlling the horizontal and vertical drive of matrix drive source 55 sets the field strengths of pixel regions 51 to adjust local refractive indexes. Thus, refractive index gradients allows a "prescription" to be programmed into lens 50, as well as variable focal lengths.

Figure 11:
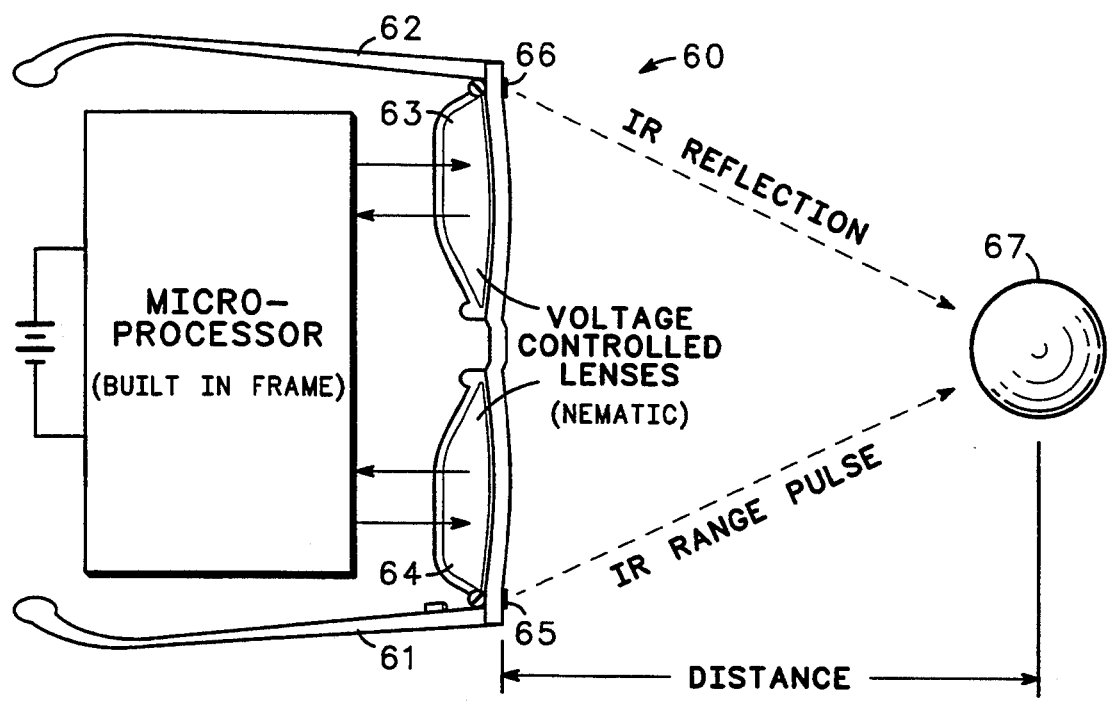
FIG. 11 is a view in top plan of an auto focusing lens system embodying the present invention.

FIG. 11 is a view in top plan of an auto focusing lens system 60 embodying the present invention. In this specific embodiment system 60 includes a set of eyeglasses 61, having eyeglass frames 62 and a pair of lenses 63 and 64. Lenses 63 and 64 are constructed similar to lens 50, described in conjunction with FIGS. 9 and 10. Electronics for driving lenses 63 and 64 are embedded in frames 61, along with an appropriate power source. It will of course be understood that the power source can be a battery embedded in frames 61, a larger battery carried somewhere else on the user and attached by small wires, a rechargeable battery and solar collectors mounted along a top surface of frames 62, etc.

Further, system 60 includes a transmitter 65 mounted in frames 61 adjacent lens 64 and a receiver 66 mounted in frames 61 adjacent lens 63. Transmitter 65 and receiver 66 form parts of a ranging system which determines the distance to an object, such as object 67, within the field of view of eyeglasses 61. It will be understood, that the ranging system can be any system utilizing transmitted and reflected energy, such as an infrared or ultrasonic system. In this specific embodiment, infrared is used for purposes of explanation, but the various components can simply be ultrasonic to convert to an ultrasonic system. Transmitter 65 transmits an infrared ranging pulse in a relatively narrow beam, which is reflected by object 67 and received by receiver 66. By locating transmitter 65 and receiver 66 at opposite sides of frames 62, sufficient distance can be achieved to prevent any direct emission. The ranging is then a simple timing of the transmission and reception of the pulse. In general, the dynamic range of system 60 is approximately 10 inches to 10 feet.

Figure 12:
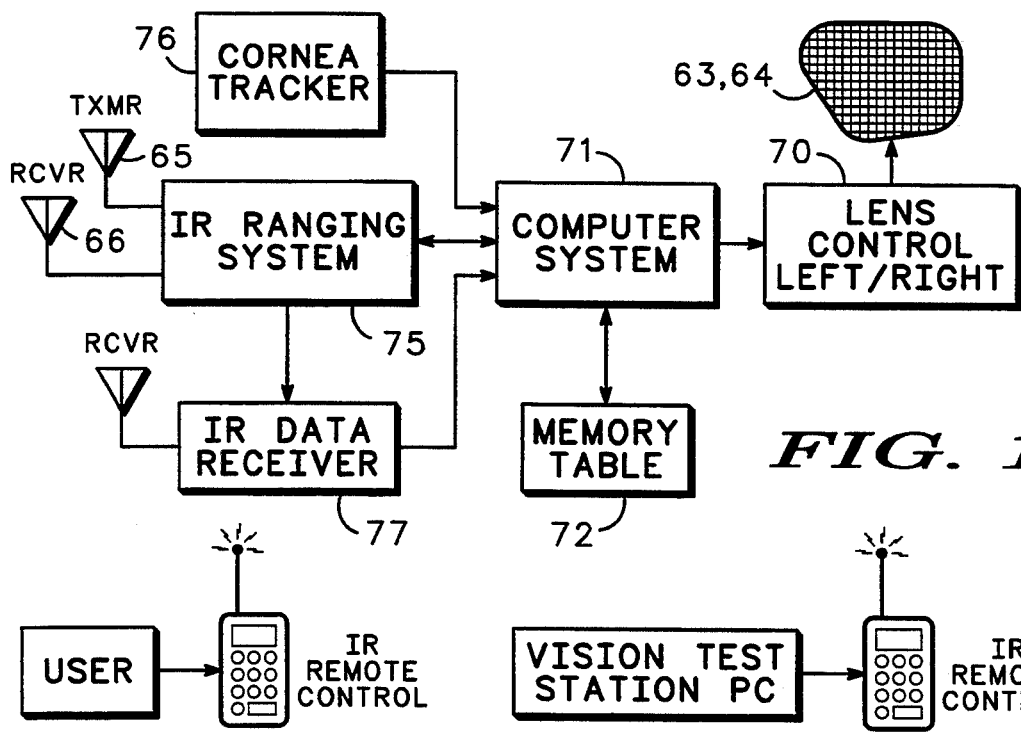
FIG. 12 is a block diagram of the electronics contained in the system of FIG. 11.

FIG. 12 is a simplified block diagram of the basic electronics in auto focusing lens system 60. Lenses 63 and 64 are controlled by lens control circuit 70, which includes a matrix drive circuit (similar to source 55). Lens control circuit 70 is in turn controlled by a computing system 71, which in this embodiment is a microprocessor. A memory 72, which may be for example a look up table stored in a ROM, RAM or the like, is associated with computer system 71. An infrared ranging system 75 is also connected to computing system 71 and to infrared transmitter 65 and infrared receiver 66. Also, in this embodiment, an optional cornea tracker 76 and an infrared data receiving system 77 are included, both of which are connected to computer system 71.

In the operation of auto focusing lens system 60, the user simply points eyeglasses 61 at an object by moving his head. Infrared transmitter 65 transmits one or more pulses (the pulse transmission may be continuous or only when the head moves sufficiently far) which are reflected from an object in the field of view and received by infrared receiver 66. Ranging system 75 measures the time from transmission to reception and quickly calculates the distance to the object. Because relatively short distances are being measured, the transmitted pulses can be very short and sharp to provide maximum accuracy. The calculations may be made in computer system 71 and then utilized to calculate signals to be provided to lens control circuit 70 for focal length adjustment of lenses 63 and 64.

In addition, secondary cornea tracking system 76 is used to measure the orientation of the eye by an infrared signal reflected from the cornea. This is a very fine grain, low power signal which, in combination with the ranging signal, provides information about the temporal location of the line of vision. In some applications, this additional refinement may not be required.

Computer system 71 utilizes the ranging signals, and the cornea tracking signals if present, to compute the required control voltages to apply to lenses 63 and 64. These voltages cause a change in the refractive index which changes the focal length of lenses 63 and 64. A bias or off set is established by the user to adjust the correct compensation for normal reading distances of 10 to 14 inches from the eye. Once established, system 60 corrects for increased distances by changing the voltage to reduce the diopter of lenses 63 and 64 for the longer distance. Since the entire lens is modified, a much wider field of view is available. Also, since system 60 is adaptive to all ranges the particular object selected is a best focus for that range. A rapid shift in focus occurs because of the closed loop control system.

Figure 13:
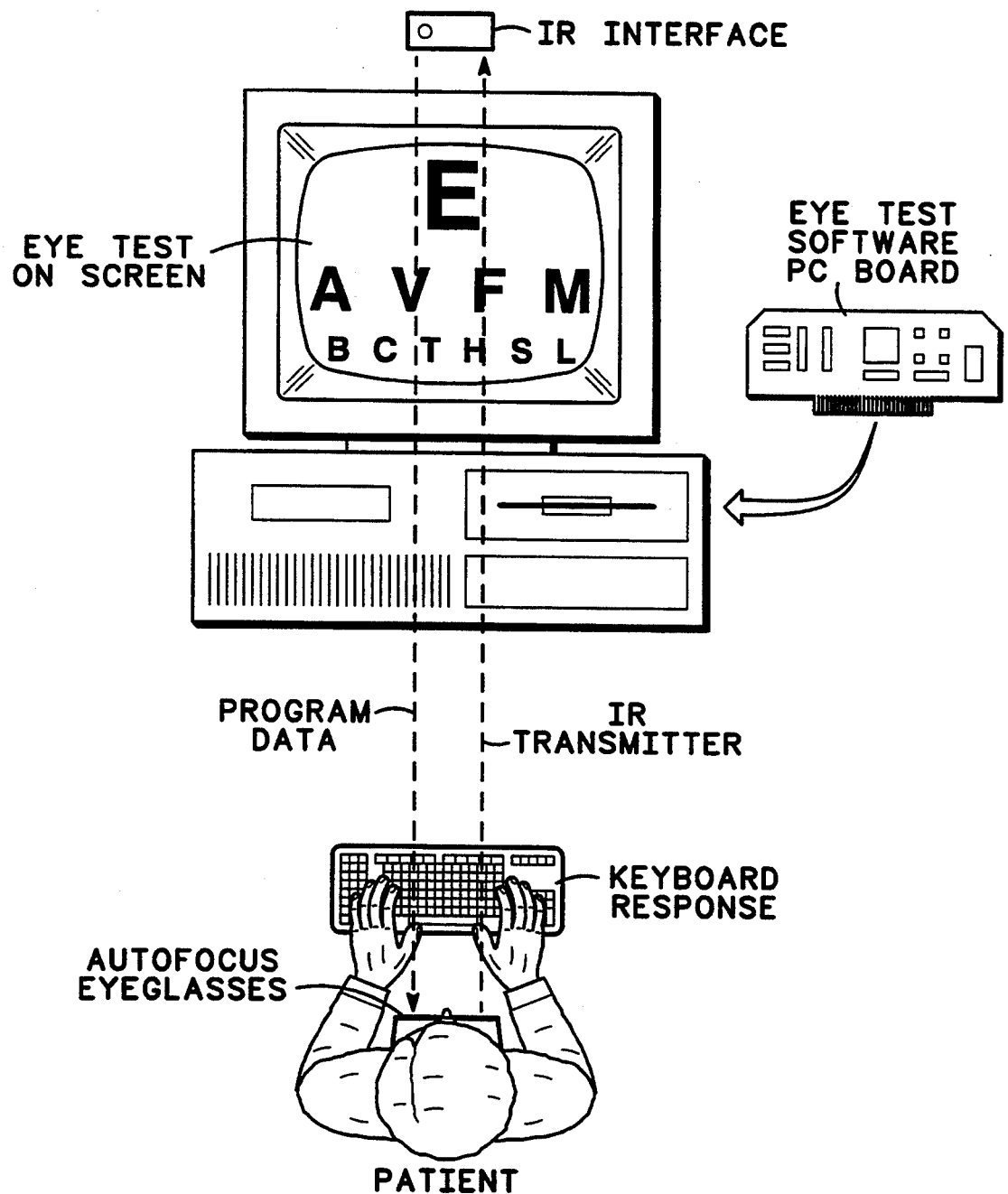
FIG. 13 illustrates a calibration station for use with the system of FIG. 11 and the general operation thereof.

Infrared data receiving system 77 allows an external test station, such as that illustrated in FIG. 13, to be used by the user to program memory 72. System 77, in this embodiment, uses (time shares) infrared receiver 66. For the system utilizing lenses formed from a plurality of cells, the computer processes signals received from the test station and stores them in look up table memory 72 for the specific user's refractive prescription. In this way localized areas of the lenses are adjusted. This is analogous to adding prism, cylinder, etc. correction to the normal spherical lens shape. These corrections are used to correct astigmatism and other vision defects. When a prescription is programmed into lenses 63 and 64 to correct specific eye problems, an algorithm is required to change the focal length of lenses 63 and 64 while retaining the refractive prescription.

While the present embodiment has been disclosed in the form of eyeglasses, for the most effective demonstration of the operation, it will be understood by those skilled in the art that many other uses and embodiments can be devised. Thus, new and improved apparatus and methods for automatically focusing optical apparatus is disclosed. Further, the new and improved apparatus and methods for automatically focusing optical apparatus operates quickly and accurately so that virtually no uncomfortable defocusing occurs. Further, the present invention includes automatically focusing and otherwise compensating eyeglasses and the like for changes in the operator's vision so that a single pair of glasses can be used for all applications and throughout a lifetime.

While we have shown and described specific embodiments of the present invention, further modifications and improvements will occur to those skilled in the art. We desire it to be understood, therefore, that this invention is not limited to the particular forms shown and we intend in the append claims to cover all modifications that do not depart from the spirit and scope of this invention.

What is claimed is:

1. Auto focusing optical apparatus comprising:
    an optical lens having a focal length determined by a refractive index thereof and containing electrically alterable material positioned to alter the refractive index of the optical lens in response to a voltage applied thereto, and a pair of electrical terminals coupled to supply an electrical field to the material and designed to have applied thereto a voltage so as to produce a predetermined alteration of the refractive index of the lens, the optical lens including a plurality of individual optically transparent, pixel regions each defined by a pair of electrically conductive transparent electrodes positioned on opposite regions of the optical lens, thereby enabling the impression of an independent electrostatic field within the pixel region;

a frame operatively mounting the optical lens;

a microprocessor mounted in the frame and connected to the electrical terminals of the optical lens, the microprocessor being programmed to automatically supply a voltage to the electrical terminals so as to produce a predetermined alteration of the refractive index of the optical lens; and a ranging system mounted in the frame and connected to the microprocessor.

2. Auto focusing optical apparatus as claimed in claim 1 wherein each pixel region of the plurality of pixel regions contains liquid crystal nematic material positioned to be electrically coupled to the electrostatic field within the pixel region and to alter the refractive index of each pixel region in response to a voltage applied to the pair of electrically conductive transparent electrodes of the pixel region.

3. Auto focusing optical apparatus comprising:

eyeglasses including a frame and a pair of optical lenses mounted in the frame;

each optical lens including an optically transparent, hollow, lens shaped shell filled with liquid crystal nematic material positioned to alter the refractive index of the optical lens in response to a voltage applied thereto, and a pair of electrical terminals coupled to the liquid crystal nematic material and designed to have applied thereto a voltage so as to produce a predetermined alteration of the refractive index of the lens;

a computer system mounted in the frame with the electrical terminals of each optical lens being connected to the computer system, the computer system being programmed to apply to the electrical terminals of each optical lens a voltage so as to produce a predetermined alteration of the refractive index of each of the optical lenses; and a ranging system mounted in the frame and connected to the computer system, the ranging system including a transmitter positioned to transmit a beam of energy onto an object in a field of view of the eyeglasses, and a receiver positioned to receive energy reflected from the object and supply an electrical signal to the computer system, the computer system being programmed to receive the electrical signal from the ranging system and convert the electrical signal into a voltage to produce an alteration of the refractive index of each of the optical lenses so as to focus each of the optical lenses on the object in the field of view.

4. Auto focusing optical apparatus as claimed in claim 3 wherein the receiver and transmitter of the ranging system include an infrared transmitter and an infrared receiver.

5. Auto focusing optical apparatus as claimed in claim 3 wherein the receiver and transmitter of the ranging system include an ultrasonic transmitter and an ultrasonic receiver.

6. Auto focusing optical apparatus as claimed in claim 3 including in addition external calibration apparatus with an interface having a transmitter and receiver mounted to communicate with the receiver and transmitter, respectively, of the eyeglasses, the computer system in the eyeglasses further including a memory and the external calibration apparatus transmitting signals to the memory in accordance with signals supplied to the calibration apparatus by a wearer of the eyeglasses.

7. Auto focusing optical apparatus comprising:

eyeglasses including a frame and a pair of optical lenses mounted in the frame;

each optical lens having a plurality of individual optically transparent, pixel regions forming a continuous lens structure, each pixel region of the plurality of pixel regions containing liquid crystal nematic material positioned to alter the refractive index of each pixel region in response to a voltage applied thereto, and each pixel region including a pair of electrical terminals coupled to the liquid crystal nematic material therein and designed to have applied thereto a voltage so as to produce a predetermined alteration of the refractive index of each pixel region, and the plurality of pixel regions in each optical lens cooperating to produce an overall refractive index for each optical lens;

a computer system mounted in the frame with the electrical terminals of each hollow cell being connected to the computer system, the computer system being programmed to apply to the electrical terminals of each cell in each optical lens a voltage so as to produce a predetermined alteration of the refractive index of each of the optical lenses; and a ranging system mounted in the frame and connected to the computer system, the ranging system including a transmitter positioned to transmit a beam of energy onto an object in a field of view of the eyeglasses, and a receiver positioned to receive energy reflected from the object and supply an electrical signal to the computer system, the computer system being programmed to receive the electrical signal from the ranging system and convert the electrical signal into a voltage to produce an alteration of the refractive index of each of the optical lenses so as to focus each of the optical lenses on the object in the field of view.

8. Auto focusing optical apparatus as claimed in claim 7 wherein the receiver and transmitter of the ranging system include an infrared transmitter and an infrared receiver.

9. Auto focusing optical apparatus as claimed in claim 8 wherein the receiver and transmitter of the ranging system include an ultrasonic transmitter and an ultrasonic receiver.

* * * * *